United States Patent
Finch et al.

(10) Patent No.: US 10,144,758 B2
(45) Date of Patent: *Dec. 4, 2018

(54) DEUTERATED BILE ACIDS

(71) Applicant: Metselex, Inc., Minneapolis, MN (US)

(72) Inventors: Michael D Finch, Apple Valley, MN (US); Walter Low, Shorewood, MN (US); Clifford Steer, Eagan, MN (US); Cyrus B. Munshi, Blaine, MN (US); Cecilia M. P. Rodrigues, Lisbon (PT); Susana Dias Lucas de Oliveira, Sao Joao de Talha (PT)

(73) Assignee: Metselex, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/651,721

(22) Filed: Jul. 17, 2017

(65) Prior Publication Data

US 2018/0030084 A1    Feb. 1, 2018

Related U.S. Application Data (63) Continuation of application No. 15/052,221, filed on Feb. 24, 2016, now Pat. No. 9,708,362, which is a continuation of application No. 14/520,889, filed on Oct. 22, 2014, now abandoned.

(60) Provisional application No. 61/894,012, filed on Oct. 22, 2013.

(51) Int. Cl.
| | | |
|---|---|---|
| *C07J 9/00* | (2006.01) | |
| *C07J 41/00* | (2006.01) | |
| *A61K 31/575* | (2006.01) | |

(52) U.S. Cl.
CPC .............. *C07J 9/005* (2013.01); *A61K 31/575* (2013.01); *C07J 41/0061* (2013.01)

(58) Field of Classification Search
CPC .......... C07J 9/00; C07J 31/006; A61K 31/575
See application file for complete search history.

(56) References Cited

U.S. PATENT DOCUMENTS

| | | | |
|---|---|---|---|
| 9,580,459 B2 * | 2/2017 | Dosa | ................... C07J 51/00 |
| 9,708,362 B2 | 7/2017 | Finch et al. | |
| 2015/0112089 A1 | 4/2015 | Finch et al. | |
| 2016/0168189 A1 | 6/2016 | Finch et al. | |

OTHER PUBLICATIONS

Amaral et al, Journal of Lipid Research, Bile acids: regulation of apoptosis by ursodeoxycholic acid, 2009, 50, pp. 121-1731. (Year: 2009).*
CRC, CRC Handbook of Chemistry and Physics, 1989, CRC Press, Inc., Boca Raton, FL, p. B-228. (Year: 1989).*
"U.S. Appl. No. 14/520,889, Final Office Action dated Aug. 25, 2015", 17 pgs.
"U.S. Appl. No. 14/520,889, Non Final Office Action dated Feb. 9, 2015", 17 pgs.
"U.S. Appl. No. 14/520,889, Response filed Jan. 23, 2015 to Restriction Requirement dated Nov. 25, 2014", 15 pgs.
"U.S. Appl. No. 14/520,889, Response filed Jun. 9, 2015 to Non Final Office Action dated Feb. 9, 2015", 16 pgs.
"U.S. Appl. No. 14/520,889, Restriction Requirement dated Nov. 25, 2014", 6 pgs.
"U.S. Appl. No. 15/052,221, Notice of Allowance dated Mar. 14, 2017", 10 pgs.
"U.S. Appl. No. 15/052,221, Response filed Jan. 18, 2017 to Restriction Requirement dated Nov. 9, 2016", 8 pgs.
"U.S. Appl. No. 15/052,221, Restriction Requirement dated Nov. 9, 2016", 6 pgs.
"CRC Handbook of Chemistry and Physics", CRC Press, Inc CRC Boca Raton, FL, (1989), B-228.
Dorwald, "Side Reactions in Organic Synthesis", A Guide of Successful Synthesis Design, Wiley: VCH, Weinhiem, (2005), 1-15.
Lai, et al., "Labeled Bile Acids Iv: Base-Catalyzed One-Pot Synthesis of Deuterium Labeled Bile Acids (1)", Journal of Labelled Compounds and Radiopharmaceuticals, (1984), 615-626.
Stroobant, et al., "Fast-atom Bombardment Mass Spectrometry and Low Energy Collision-induced Tandem Mass spectrometry of Tauro Conjugated Bile Acid Anions", Journal of the American Society for Mass Spectrometry, (1995), 588-596.

* cited by examiner

*Primary Examiner* — Paul A Zucker
(74) *Attorney, Agent, or Firm* — Schwegman Lundberg & Woessner, P.A.

(57) ABSTRACT

This disclosure relates to deuterated bile acid compositions. A deuterated compound is selected from the bile acids such as ursodeoxycholic acid (UDCA) and tauroursodeoxycholic acid (TUDCA), and their derivatives, analogs and salts. At least one of the hydrogen atoms in the compound is replaced with deuterium. Also disclosed are pharmaceutical compositions and methods of using the deuterated bile acids.

6 Claims, 8 Drawing Sheets

DEUTERATED BILE ACIDS

CROSS-REFERENCE TO RELATED APPLICATION(S)

This application is a continuation of U.S. application Ser. No. 14/520,889, now U.S. Pat. No. 9,708,362, filed Oct. 22, 2014, and entitled "DEUTERATED BILE ACIDS", which claims priority from U.S. Provisional Application Ser. No. 61/894,012, filed Oct. 22, 2013, and entitled "DEUTERATED BILE ACIDS".

BACKGROUND

Ursodeoxycholic acid (UDCA) and tauroursodeoxycholic acid (TUDCA) are anti-apoptotic molecules with protective effects against several neurodegenerative disorders such as Alzheimer's and Parkinson's diseases as well as against acute kidney injury. Both UDCA and TUDCA block the initiating event of the apoptotic process, in part, through stabilizing the mitochondrial membrane potential, a mechanism that enhances the integrity of the mitochondria. Enhanced mitochondrial integrity abolishes the release of several mitochondrial proteins such as cytochrome C into the cytosol, thereby preventing the onset of apoptosis. Further, UDCA and TUDCA upregulate several pathways that function synergistically with their anti-apoptotic properties.

The kinetic deuterium isotope effect (KDIE) is a function of enhanced carbon-deuterium (C-D) bond strength over the carbon-hydrogen (C—H) bond, often several-fold. Substitution of the C—H by the C-D bond significantly decreases breakage, thereby increasing the resident time of the molecule in the body. Therefore, substituting one or more of the carbons with deuterium significantly increases the metabolic clearance time. An added benefit of the KDIE is the possibility of using lower dosages to derive the same pharmacological effect. The C-D bond is twice as strong as the C—H bond by virtue of a two-fold higher mass of deuterium over hydrogen. Hence, the reaction rate of the C-D bond breakage is significantly slower than that of the C—H bond breakage.

SUMMARY

This disclosure relates to deuterated bile acid compositions. A deuterated compound is selected from the disclosed groups of bile acids and their derivatives, analogs and salts. At least one of the hydrogen atoms in the compound is replaced with deuterium.

DETAILED DESCRIPTION

This patent application pertains to the field of pharmaceutical molecules and specifically to deuterated versions of bile acids, such as UDCA and TUDCA as well as their analogs and derivatives, with enhanced resident time following administration to a patient.

Deuteration of bile acids can significantly increase the half-life of the drug in the bloodstream and, hence, decrease the dosage needed to treat various degenerative disorders. Disclosed herein are various compositions of deuterated bile acids and their analogs and derivatives, as well as methods of preparation.

Figure 1:
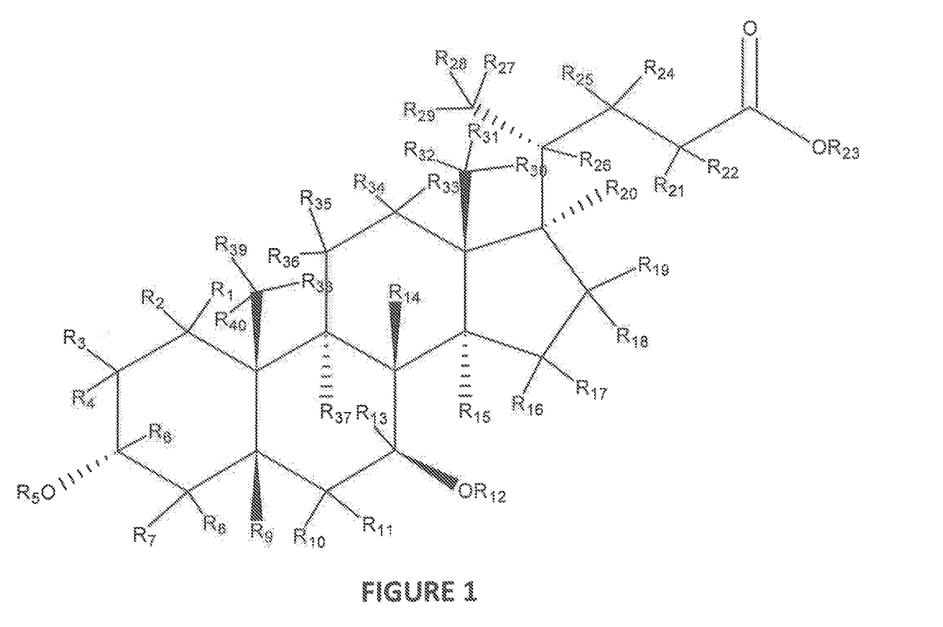
FIG. 1 illustrates the structure of UDCA.

In some embodiments, UDCA, its analogs and salts have the structure of Formula I as illustrated in FIG. 1 and reproduced below:

Formula I

Deuterated UDCA where $R_1$-$R_{40}$ are individual hydrogen or deuterium atoms. Any analog or salt of UDCA can contain at least one deuterium atom represented by any of the $R_1$-$R_{40}$ locations in any combination.

In another embodiment of formula I, the deuterated UDCA or UDCA analog is a salt containing one or more $PO_4$ groups, preferably in positions 3, 7, 24.

Figure 2:
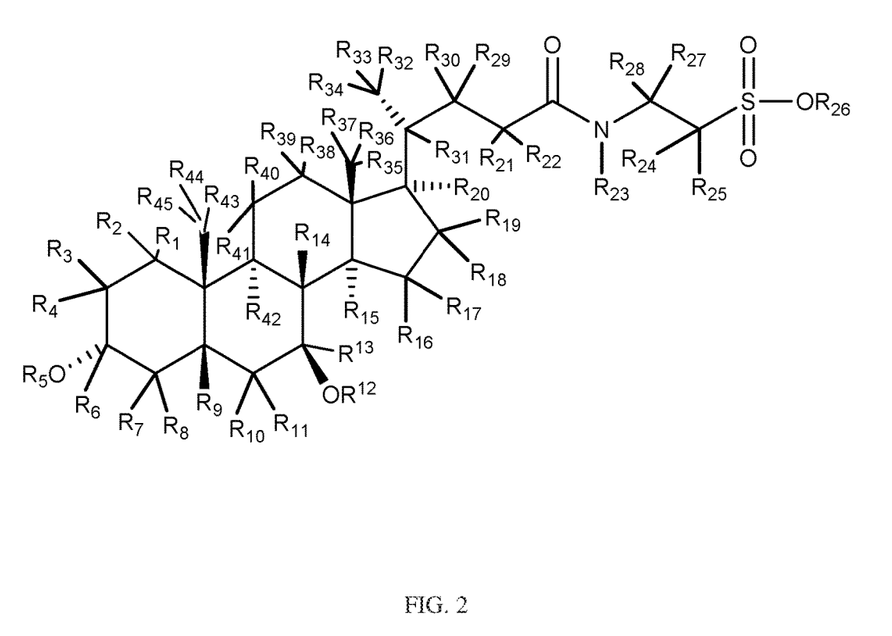
FIG. 2 illustrates the structure of TUDCA.

In other embodiments, TUDCA, its analogs and salts have the structure of Formula II as illustrated in FIG. 2 and reproduced below:

where $R_1$-$R_{45}$ are individual hydrogen or deuterium atoms. Any analog or salt of TUDCA can contain at least one deuterium atom represented by any of the $R_1$-$R_{45}$ locations in any combination.

In another embodiment of Formula II, the deuterated TUDCA or TUDCA analog is a salt containing one or more $PO_4$ groups, preferably in positions 3, 7, 24.

Figure 3:
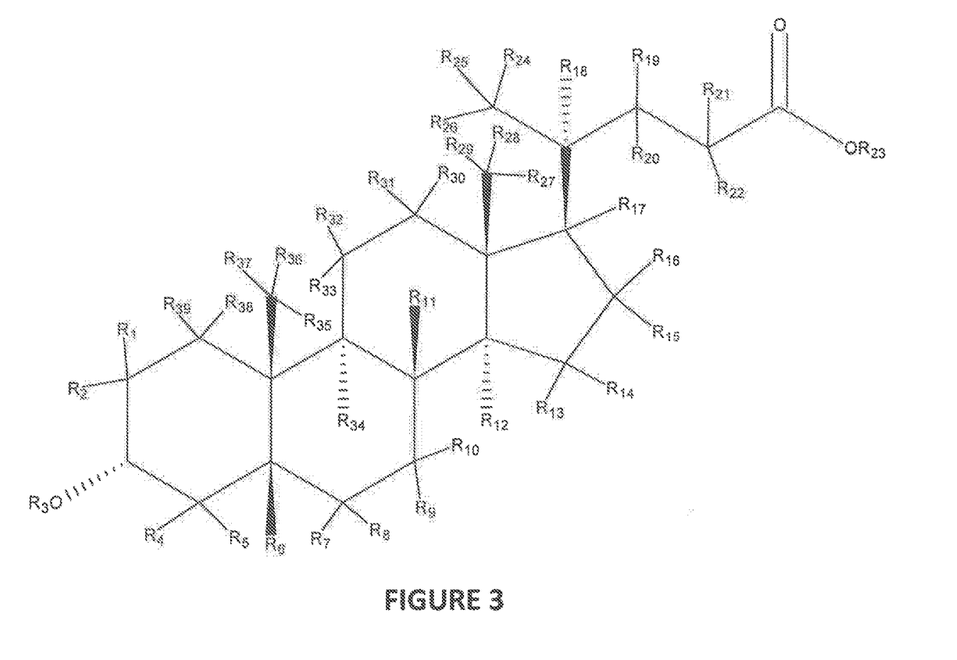
FIG. 3 illustrates the structure of lithocholic acid (LCA).

In other embodiments, lithocholic acid (LCA), its salts, derivatives and analogs have the structure of Formula III as illustrated in FIG. 3 and reproduced below:

Formula III

Deuterated Lithocholic acid where $R_1$-$R_{39}$ are individual hydrogen or deuterium atoms. Any analog or salt of LCA can contain at least one deuterium atom represented by any of the $R_1$-$R_{39}$ locations in any combination.

In another embodiment of Formula III, the deuterated LCA or LCA analog is a salt containing one or more $PO_4$ groups, preferably in positions 3, 7, 24.

Figure 4:
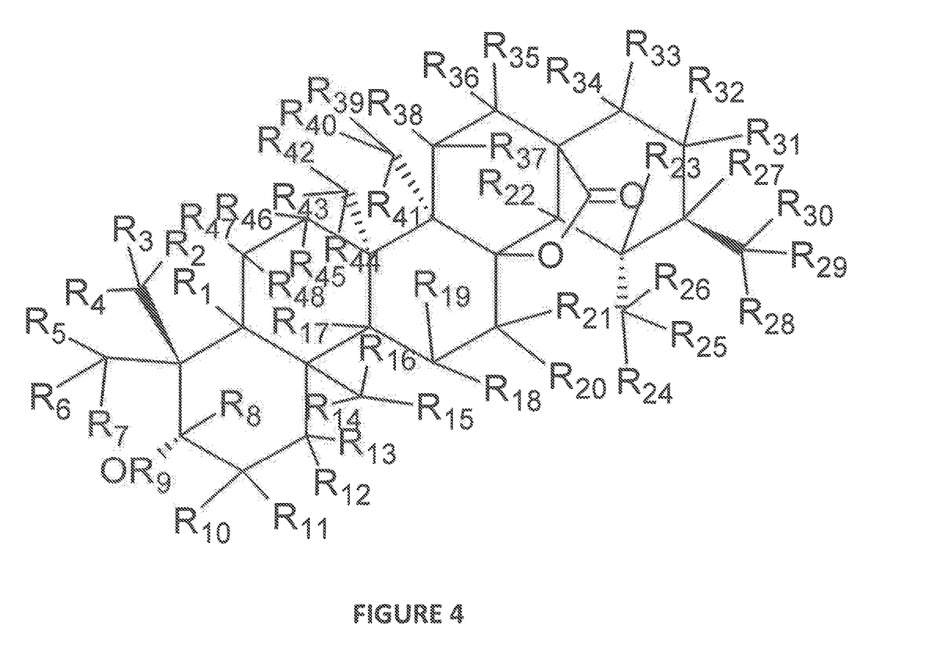
FIG. 4 illustrates the structure of dehydro(11,12)ursolic acid lactone.

In other embodiments, dehydro-(11,12)-ursolic acid lactone, its salts, derivatives and analogs have the structure of Formula IV as illustrated in FIG. 4 and reproduced below:

Formula IV

Deuterated dehydro-(11,12)-ursolic acid lactone where $R_1$-$R_{48}$ are individual hydrogen or deuterium atoms. Any analog, derivative or salt of dehydro-(11,12)-ursolic acid lactone can contain at least one deuterium atom represented by any of the $R_1$-$R_{48}$ locations in any combination.

In another embodiment of Formula IV, the analog or derivative of dehydro-(11,12)-ursolic acid lactone is a salt containing one or more $PO_4$ groups.

Figure 5:
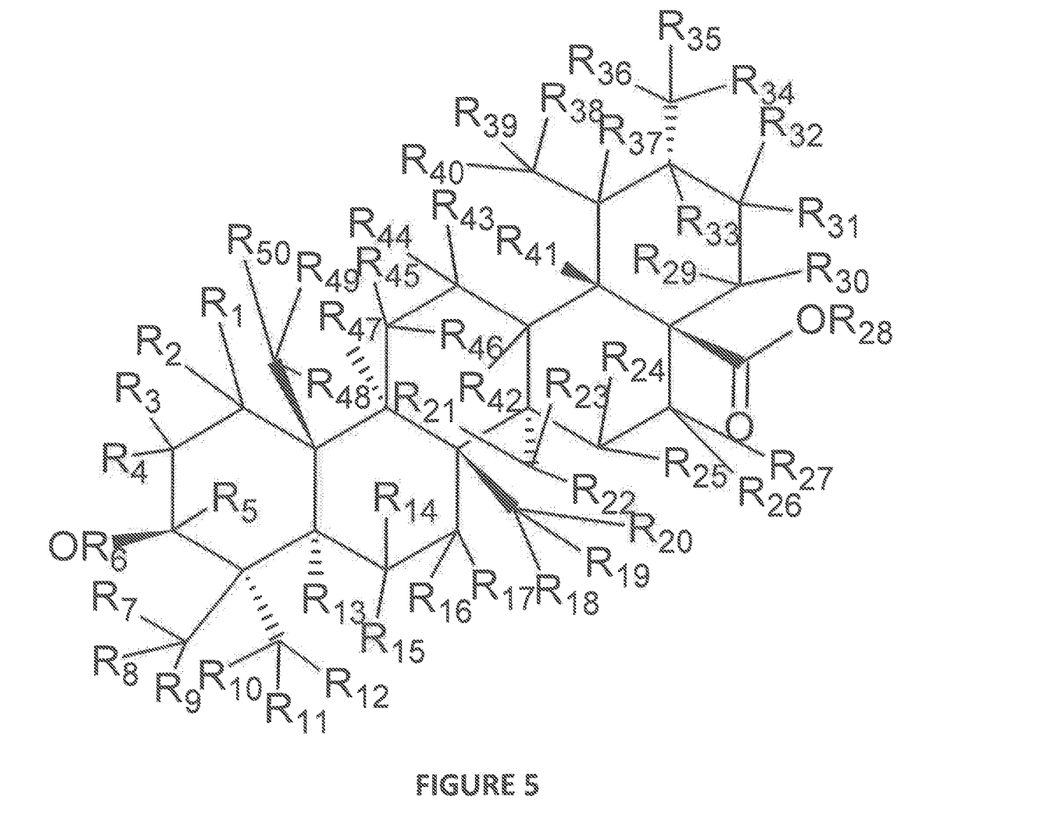
FIG. 5 illustrates the structure of ursolic acid.

In other embodiments, ursolic acid, its salts, derivatives and analogs have the structure of Formula V as illustrated in FIG. 5 and reproduced below:

Formula V

Deuterated ursolic acid where $R_1$-$R_{50}$ are individual hydrogen or deuterium atoms. Any analog, derivative or salt of ursolic acid can contain at least one deuterium atom represented by any of the $R_1$-$R_{50}$ locations in any combination.

In another embodiment of Formula V, the analog or derivative of ursolic acid is a salt containing one or more $PO_4$ groups.

Figure 6:
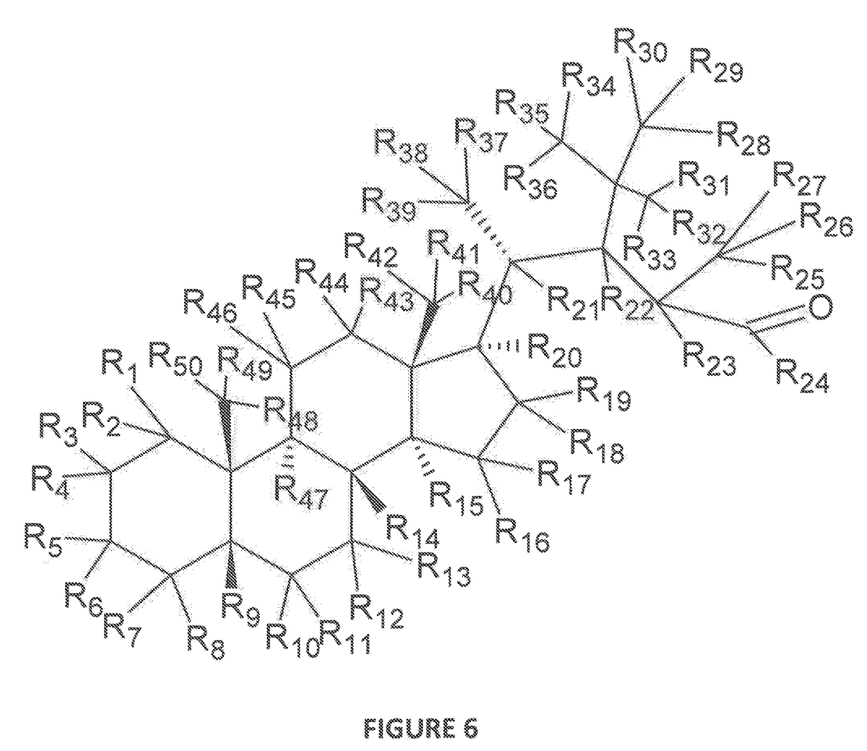
FIG. 6 illustrates the structure of ursocholanic acid.

In other embodiments, ursocholanic acid, its salts, derivatives and analogs have the structure of Formula VI as illustrated in FIG. 6 and reproduced below:

Formula VI

Deuterated usrocholanic acid where $R_1$-$R_{50}$ are individual hydrogen or deuterium atoms. Any analog, derivative or salt of ursocholanic acid can contain at least one deuterium atom represented by any of the $R_1$-$R_{50}$ locations in any combination.

In another embodiment of Formula VI, the analog or derivative of ursocholanic acid is a salt containing one or more $PO_4$ groups.

In another embodiment, structures with formulae I, II, III, IV, V, and VI, and all derivatives thereof are conjugated to any anti-neurodegenerative pro-drug molecules involved in modulating neuronal apoptosis.

In another embodiment, structures with formulae I, II, III, IV, V, and VI, and all derivatives thereof are conjugated to pro-drugs of dopaminergic neurons (DA) neurons such as L-DOPA ((S)-2-Amino-3-(3,4-dihydroxyphenyl)propanoic acid) and any analog of L-DOPA.

In another embodiment, structures with formulae I, II and III and all derivatives thereof are conjugated to glutamate receptor antagonists.

In another embodiment, structures with formulae I, II, III, IV, V, and VI, and all derivatives thereof are conjugated to antioxidants.

In another embodiment, structures with formulae I, II, III, IV, V, and VI, and all derivatives thereof are combined, without conjugation, to any anti-neurodegenerative pro-drug molecules involved in modulating neuronal apoptosis.

In another embodiment, structures with formulae I, II, III, IV, V, and VI, and derivatives thereof are combined, without conjugation, to any anti-neurodegenerative pro-drugs of DA neurons such as L-DOPA and any analog of L-DOPA.

In another embodiment, structures with formulae I, II, III, IV, V, and VI, and derivatives thereof are combined, without conjugation, to glutamate receptor antagonists.

In another embodiment, structures with formulae I, II, III, IV, V, and VI, and derivatives thereof are combined, without conjugation, to antioxidants.

Typically, for some embodiments, the compound described herein can be formulated in pharmaceutical compositions. A pharmaceutical composition containing a compound of the present disclosure can be administered to a subject, typically a mammal such as a human subject, in a variety of forms adapted to the chosen route of administration. The formulations include those suitable for in vitro cell culture as well as oral, rectal, vaginal, topical, nasal, ophthalmic, parenteral (including subcutaneous, intramuscular, intraperitoneal, intravenous, intrathecal, intraventricular, direct injection into brain tissue, etc.) administration.

The formulations can be conveniently presented in unit dosage form and can be prepared by any of the methods well known in the art of pharmacy. Typically, such methods include the step of bringing the active compound into association with a carrier, which can include one or more accessory ingredients. In general, the formulations are prepared by uniformly and intimately bringing the active compound into association with a liquid carrier, a finely divided solid carrier, or both, and then, if necessary, shaping the product into a desired formulation.

Formulations of the present disclosure suitable for oral administration can be presented as discrete units such as tablets, troches, capsules, lozenges, wafers, or cachets, each containing a predetermined amount of the described apoptosis-limiting compound as a powder, in granular form, incorporated within liposomes, or as a solution or suspension in an aqueous liquid or non-aqueous liquid such as a syrup, an elixir, an emulsion, or a draught.

The tablets, troches, pills, capsules, and the like can also contain one or more of the following: a binder such as gum tragacanth, acacia, corn starch, or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it can further contain a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, sugar, and the like. A syrup or elixir can contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The compound can be incorporated into sustained-release preparations and devices, if desired.

A compound suitable for use in the methods of the disclosure can also be incorporated directly into the food of a subject's diet, as an additive, supplement, or the like. Thus, the disclosure further provides a food product. Any food can be suitable for this purpose, although processed foods already in use as sources of nutritional supplementation or fortification, such as breads, cereals, milk, and the like, are convenient to use for this purpose.

Formulations suitable for parenteral administration conveniently include a sterile aqueous preparation of the desired compound, or dispersions of sterile powders having the desired compound, which are preferably isotonic with the blood of the subject. Isotonic agents that can be included in the liquid preparation include sugars, buffers, and salts such as sodium chloride. Solutions of the desired compound can be prepared in water, optionally mixed with a nontoxic surfactant. Dispersions of the desired compound can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the desired compound, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thiomersal (Ethyl(2-mercaptobenzoato-(2-)-O,S)mercurate(1-) sodium), and the like. Absorption of the desired compounds over a prolonged period can be achieved by including agents for delaying, for example, aluminum monostearate and gelatin.

Nasal spray formulations can include purified aqueous solutions of the desired compound with preservative agents and isotonic agents. Such formulations are preferably adjusted to a pH and isotonic state compatible with the nasal mucous membranes. Ophthalmic formulations are prepared by a similar method to the nasal spray, except that the pH and isotonic factors are preferably adjusted to match that of the eye. Formulations for rectal or vaginal administration can be presented as a suppository with a suitable carrier such as cocoa butter, or hydrogenated fats or hydrogenated fatty carboxylic acids.

In addition, a compound of the present disclosure can be modified by appropriate functionalities to enhance selective biological properties. Such modifications are known in the art and include those which increase biological penetration into a given biological system (e.g., blood, lymphatic system, central nervous system, brain), increase oral availability, increase solubility to allow administration by injection, alter metabolism and alter rate of exertion. In addition, a compound can be altered to pro-drug form such that the desired compound is created in the body of the subject as the result of the action of metabolic or other biochemical processes on the pro-drug. Some examples of pro-drug forms include ketal, acetal, oxime, and hydrazone forms of a compound that contains ketone or aldehyde groups.

Preferably, when a compound of the present disclosure can be delivered in vivo, the dosage level of the compound is on the order of about 10 milligrams to about 15 milligrams per kilogram of body weight per day. Preferably, the effective amount is on the order of about 500 milligrams to about 1000 milligrams per subject per day. When a compound of the present disclosure is delivered to a subject, the compound can be delivered in one or multiple dosages for injection, infusion, and/or ingestion.

Deuterated compounds according to the present disclosure can have various levels of deuterium enrichment. Deuterium enrichment is defined as the percentage of $R_1$-$R_{xx}$ groups having deuterium atoms. In one embodiment, the deuterated compound has deuterium enrichment of at least 5%. In another embodiment, the deuterated compound has deuterium enrichment of at least 10%. In another embodiment, the deuterated compound has deuterium enrichment of at least 30%. In another embodiment, the deuterated compound has deuterium enrichment of at least 50%. In another embodiment, the deuterated compound has deuterium enrichment of at least 70%. In another embodiment, the deuterated compound has deuterium enrichment of at least 98%. In another embodiment, the deuterated compound has the structure of formula I and has deuterium enrichment of at least 90%. Determination of the level of deuterium enrichment can be performed by mass spectrometry or nuclear magnetic resonance evaluation.

EXAMPLES

Synthesis of 7,8-[$^2$H]-3α,7α-dihydroxy-5β-cholan-24-oic acid/7-[$^2$H]-3α,7α-dihydroxy-5β-cholan-24-oic acid (5a,b)

General Methods:

All reagents were purchased from Sigma-Aldrich Corp. (St. Louis, Mo., USA) and used without further purification unless otherwise noted. Reactions were followed by thin layer chromatography (TLC), carried out using Merck aluminum backed sheets coated with 60 F254 silica gel, using EtOAc or EtOAc/n-Hexane mixtures as eluent. Visualization of the TLC spots was achieved by spraying with a 10% solution of sulfuric acid in methanol followed by heating. Silica gel was acquired from Merck & Co. (White House Station, N.J., USA; 60 G, 0.040-0.063 mm).

$^1$H— and spectra were recorded on a Bruker Avance III (300 and 100 MHz, respectively). All chemical shifts are quoted on the δ scale in ppm using residual solvent peaks as the internal standard. Coupling constants (J) are reported in Hz with the following splitting abbreviations: s=singlet, d=doublet, t=triplet, m=multiplet.

Synthesis of Methyl-3α,7α-dihydroxy-5β-cholanoate (Compound 2)

To a solution of commercial 3α,7α-dihydroxy-5β-cholanic acid (500 mg, 1.27 mmol) in MeOH (40 mL) was added p-toluenosulfonic acid and the mixture was refluxed under nitrogen atmosphere for 2 hours. The reaction mixture was poured into water (100 mL) and the product was extracted with EtOAc (3×50 mL). The organics were combined, dried over anhydrous sodium sulfate, filtered and concentrated in the rotary evaporator to yield a colorless oil (516 mg, 1.27 mmol, quantitative yield). The residue was pure as judged by TLC and was reacted without further purification.

Synthesis of Methyl-3α-hydroxy-7-oxo-5β-cholanoate (Compound 3)

To a solution of methyl-3α,7α-dihydroxy-5β-cholanoate (Compound 2; 500 mg, 1.23 mmol) in CHCl$_3$ (30 mL, anhydrous) was added silica-gel (2 g) and to this suspension was then added pyridinium chlorochromate (300 mg, 1.38 mmol). The reaction was stirred at room temperature for 5 hours under nitrogen atmosphere. Et$_2$O was added (100 mL) and the suspension was filtered over a silica-gel column eluting with Et$_2$O/DCM (7/3) to afford the desired product as a colorless solid (309 mg, 62%). MS (ESI+): m/z 427.1 [M+Na]$^+$. By-product methyl-3,7-di-oxo-5β-cholanoate was obtained as a colorless solid (154 mg, 31%). MS (ESI+): m/z 425.2 [M+Na]$^+$.

Synthesis of 3α-hydroxy-7-oxo-5β-cholan-24-oic acid (Compound 4)

To a solution of methyl-3α-hydroxy-7-oxo-5β-cholanoate (Compound 3; 269 mg, 0.66 mmol) in THF was added LiOH (12 mL, 0.3M aqueous soln) and the mixture was stirred at room temperature for 4 hours. The mixture was acidified with 1M HCl until pH 1 and the product extracted with EtOAc (3×30 mL). The organics were combined, dried over anhydrous sodium sulfate, filtered and concentrated in the rotatory evaporator to yield a crystalline solid (192 mg, 0.49 mmol, 74%). MS (ESI+): m/z 413.2 [M+Na]$^+$. $^1$H NMR (300 MHz, MeOD) δ 3.60-3.46 (m, 1H), 2.99 (m, 1H), 2.54 (t, J=11.2 Hz, 1H), 2.34 (m, 1H), 2.26-2.10 (m, 2H), 2.09-1.71 (m, 7H), 1.71-1.25 (m, 9H), 1.25-0.99 (m, 8H), 0.96 (d, J=6.5 Hz, 3H), 0.71 (s, 3H).

Synthesis of 7,8-[$^2$H]-3α,7α-dihydroxy-5β-cholan-24-oic acid (Compound 5a)/7-[$^2$H]-3α,7α-dihydroxy-5β-cholan-24-oic acid (Compound 5b) (65/35 isotopic ratio)

To a refluxing solution of 3α-hydroxy-7-oxo-5β-cholic acid (Compound 4; 59 mg, 0.15 mmol) in $^i$propan(ol-d) (6 mL) in nitrogen atmosphere, was added potassium metal (ca. 100 mg) in small pieces and the mixture was refluxed for 45 minutes. A 1M HCl soln was carefully added (up to 20 mL) and the product was extracted with EtOAc (3×10 mL). The organics were combined, dried over anhydrous sodium sulfate, filtered and concentrated in the rotatory evaporator. The product was recrystallized with EtOAc/n-Hexane to yield a colorless solid (Compound 5a,b; 46 mg, 78%). MS (ESI−): m/z 393.0 [M(1D)−1]$^−$ (35%); 393.0 [M(2D)−1]$^−$ (65%). $^1$H NMR (300 MHz, MeOD) δ 3.44-3.57 (m, 1H), 2.15-2.40 (m, 2.4H), 2.02-2.07 (m, 1H), 1.79-1.92 (m, 5H), 1.56-1.63 (m, 3H), 1.08-1.53 (m, 15 H), 0.87-1.03 (m, 5H), 0.72 (s, 3H). Compound 5 is a mixture of Compound 5a (7,8-[$^2$H]-3α,7α-dihydroxy-5β-cholan-24-oic acid) and Compound 5b (7-[$^2$H]-3α,7α-dihydroxy-5β-cholan-24-oic acid).

Cell Culture and Treatments

Primary rat hepatocytes were isolated from male rats (100-150 grams) by collagenase perfusion (as described by Solá S, et al., 2003, *Journal of Biological Chemistry* 278: 48831-48838)). Briefly, rats were anesthetized with phenobarbital sodium (100 mg/kg body weight) injected into the peritoneal cavity. After administration of heparin (200 units/kg body weight) in the tail vein, the animal's abdomen was opened and the portal vein exposed and cannulated. The liver was then perfused at 37° C. in situ with a calcium-free Hanks' Balanced Salt Solution (HBSS) for about 10 minutes, and then with 0.05% collagenase type IV in calcium-present HBSS for another 10 minutes. Hepatocyte suspensions were obtained by passing collagenase-digested livers through 125 μm gauze and washing cells in Complete William's E medium (William's E medium, Sigma-Aldrich Corp., St Louis, Mo., USA) supplemented with 26 mM sodium bicarbonate, 23 mM HEPES, 0.01 units/mL insulin, 2 mM L-glutamine, 10 nM dexamethasone, 100 units/mL penicillin, and 10% heat-inactivated fetal bovine serum (Invitrogen Corp., Carlsbad, Calif., USA). Viable primary rat hepatocytes were enriched by low-speed centrifugation at 200 g for 3 minutes. Cell viability was determined by trypan blue exclusion and was typically 80-85%. After isolation, hepatocytes were resuspended in Complete William's E medium and plated on Primaria™ tissue culture dishes (BD Biosciences, San Jose, Calif., USA) at 5×10$^4$ cells/cm$^2$. Cells were maintained at 37° C. in a humidified atmosphere of 5% CO$_2$ for 6 hours to allow attachment. Plates were then washed with medium to remove dead cells and incubated in Complete William's E medium supplemented with either 100-400 μM UDCA (Sigma-Aldrich Corp.), 100-400 μM deuterated UDCA (compound 5), or no addition (control). Eight hours after pre-incubation, cells were exposed to 1 nM recombinant human TGF-β1 (R&D Systems Inc., Minneapolis, Minn., USA) for 36 hours, or to 50 or 100 μM DCA for 16 hours before processing for cell viability, cytotoxicity and apoptosis assays.

Cell Viability, Cytotoxicity, and Caspase Activity Assays

The ApoTox-Glo™ Triplex Assay (Promega Corp., Madison, Wis., USA) was used to evaluate cell viability, cytotoxicity and caspase-3/7 activity, according to the manufacturer's protocol, using a GloMax+ Multi Detection System (Promega Corp.). General cell death was also evaluated using the lactate dehydrogenase (LDH) Cytotoxicity Detection Kit$^{PLUS}$ (Roche Diagnostics GmbH, Mannheim, Germany), following the manufacturer's instructions.

Morphologic Evaluation of Apoptosis

Hoechst labeling of cells was used to detect apoptotic nuclei by morphological analysis. Briefly, culture medium was gently removed to prevent detachment of cells. Attached primary rat hepatocytes were fixed with 4% paraformaldehyde in phosphate-buffered saline (PBS), pH 7.4, for 10 minutes at room temperature, washed with PBS, incubated with Hoechst dye 33258 (Sigma-Aldrich Corp.) at 5 μg/mL in PBS for 5 minutes, washed with PBS, and mounted using Fluoromount-GTM (SouthernBiotech, Birmingham, Ala., USA). Fluorescence was visualized using an Axioskop fluorescence microscope (Carl Zeiss GmbH). Blue-fluorescent nuclei were scored blindly and categorized according to the condensation and staining characteristics of chromatin. Normal nuclei showed non-condensed chromatin dispersed over the entire nucleus. Apoptotic nuclei were identified by condensed chromatin, contiguous to the nuclear membrane, as well as by nuclear fragmentation of condensed chromatin. Five random microscopic fields per sample containing approximately 150 nuclei were counted, and mean values expressed as the percentage of apoptotic nuclei.

Statistical Analysis

Statistical analysis was performed using GraphPad InStat version 3.00 (GraphPad Software, San Diego, Calif., USA) for the analysis of variance and Bonferroni's multiple comparison tests. Values of p<0.05 were considered significant.

Results

Figure 7:
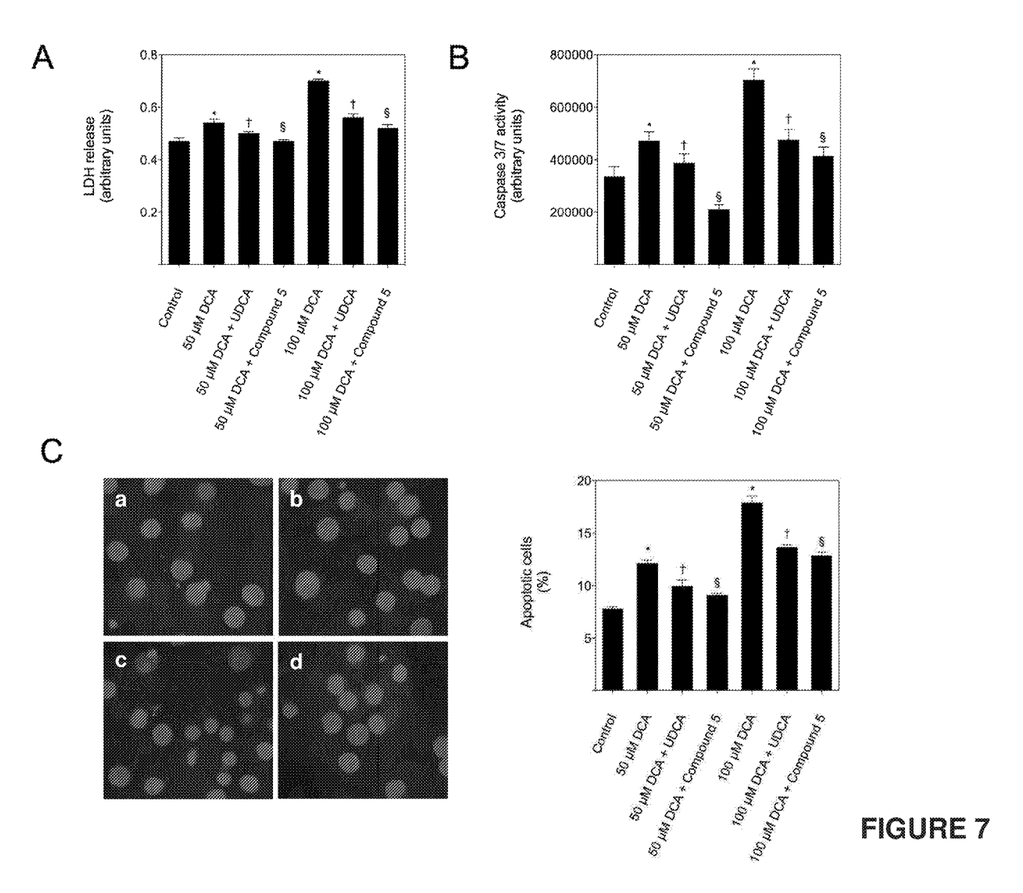
FIG. 7 illustrates the effect of deuterated UDCA on DCA-induced cytotoxicity and apoptosis in primary rat hepatocytes.
Figure 8:
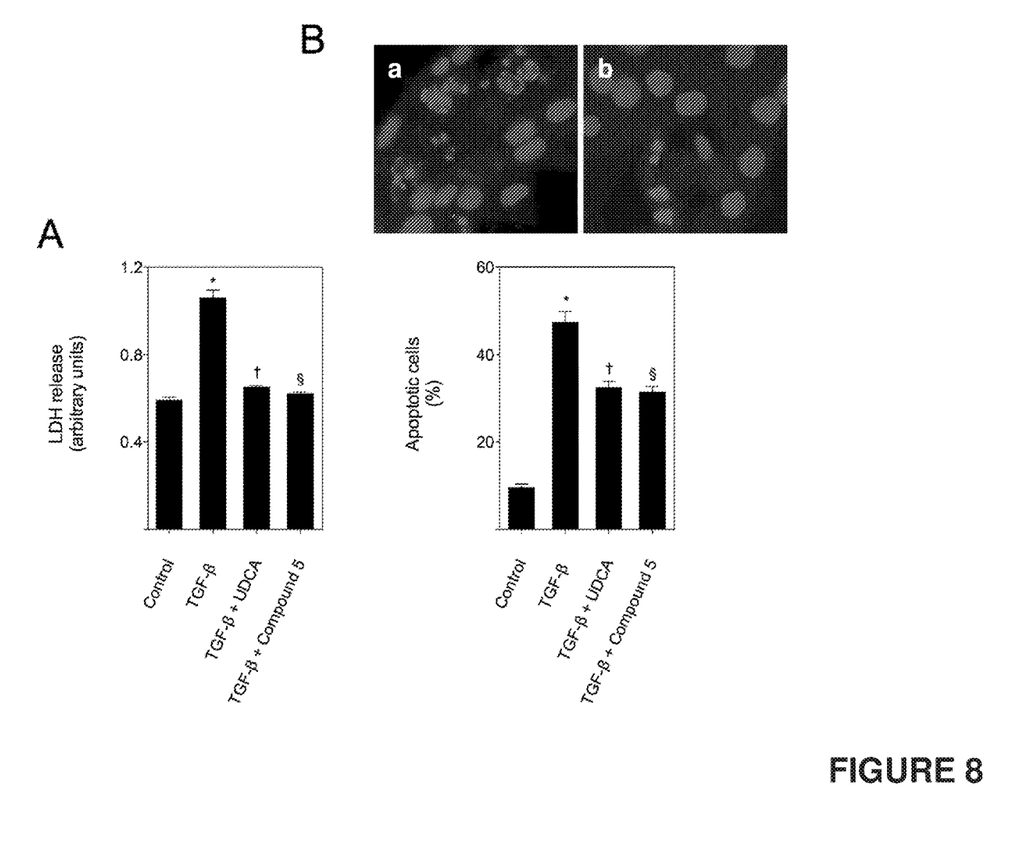
FIG. 8 illustrates the effect of deuterated UDCA on TGF-β1-induced cytotoxicity and apoptosis in primary rat hepatocytes.

We tested the cytoprotective and anti-apoptotic effects of newly synthesized deuterated UDCA (Compound 5), using well-established cellular models of apoptosis. It has been previously shown that non-deuterated UDCA significantly inhibits DCA-induced apoptosis by ~60% (Castro et al., 2007, *American Journal of Physiology Gastrointestinal Liver Physiology* 293: G327-G334) and TGF-β1-induced apoptosis by ~50% (Solá et al., 2003) in primary rat hepatocytes. Cells exposed to 100 and 200 μM concentrations of Compound 5 alone showed no relevant signs of cytotoxicity. Nevertheless, a ~2% and 15% increase in cytotoxicity was observed in cells incubated with the highest concentration of 400 μM Compound 5 for 24 and 44 hours, respectively. This was comparable to UDCA cytotoxicity. In dissecting the cytoprotective effects of Compound 5, we tested its ability to prevent DCA-induced cytotoxicity and apoptosis, as compared with UDCA. UDCA and Compound 5 inhibited 50 μM DCA-induced LDH release by 70 and 90%, respectively (FIG. 7A). This protective effect was more than 10% greater for Compound 5 as compared to UDCA. Slightly reduced protection was obtained for both UDCA and Compound 5 in cells exposed to 100 μM DCA. Notably, Compound 5 pretreatment was more effective than UDCA at markedly inhibiting caspase activity in cells exposed to both 50 and 100 μM DCA (FIG. 7B). Similar results were obtained after evaluating nuclear morphology and counting apoptotic nuclei. Nuclear fragmentation induced by 50 μM DCA was prevented by ~50% and 65% in cells pretreated with UDCA and Compound 5, respectively (FIG. 7C). Compound 5 was ~15% more effective than UDCA at reducing the percentage of apoptotic cells. Finally, in cells exposed to a stimulus unrelated to bile acids, Compound 5 was about 10% more effective than UDCA at inhibiting TGF-β1-induced LDH release, which in turn was very significantly abrogated (FIG. 8A). In addition, the percentage of apoptotic cells was reduced by almost 40% after UDCA and Compound 5 pre-treatment (FIG. 8B). Altogether, these results show that Compound 5 displays powerful cytoprotective and anti-apoptotic properties in vitro that may even exceed those of UDCA.

FIG. 7 illustrates that Compound 5 prevents DCA-induced cytotoxicity and apoptosis in primary rat hepatocytes. Primary rat hepatocytes were incubated with 100 μM UDCA, Compound 5, or no addition (control) for 8 hours. Cells were then exposed to 50 or 100 μM DCA for 16 hours before processing for LDH activity (A), caspase-3/7 activity (B) and nuclear fragmentation assays (C). Fluorescent microscopy of Hoechst staining in cells exposed to either DCA 50 μM (a), DCA 50 μM+Compound 5 (b), DCA 100 μM (c), or DCA 100 μM+Compound 5 (d). Normal nuclei showed non-condensed chromatin dispersed over the entire nucleus. Apoptotic nuclei were identified by condensed chromatin, contiguous to the nuclear membrane, as well as nuclear fragmentation of condensed chromatin. Results are expressed as means±SEM of at least three experiments. *p<0.01 from control; § p<0.05 and †p<0.01 from respective DCA.

FIG. 8 illustrates that Compound 5 prevents TGF-β1-induced cytotoxicity and apoptosis in primary rat hepatocytes. Primary rat hepatocytes were incubated with 100 μM UDCA, Compound 5, or no addition (control) for 8 hours. Cells were then exposed to 1 nM TGF-β1 for 36 hours before processing for LDH activity (A), caspase-3/7 activity (B) and nuclear fragmentation assays (C). Fluorescent microscopy of Hoechst staining in cells exposed to either TGF-β1 (a) or TGF-β1+Compound 5 (b). Normal nuclei showed noncondensed chromatin dispersed over the entire nucleus. Apoptotic nuclei were identified by condensed chromatin, contiguous to the nuclear membrane, as well as nuclear fragmentation of condensed chromatin. Results are expressed as means±SEM of at least three experiments. *p<0.01 from control; § p<0.05 and †p<0.01 from TGF-β1.

Although the present invention has been described with reference to preferred embodiments, workers skilled in the art will recognize that changes may be made in form and detail without departing from the spirit and scope of the invention.

The invention claimed is:

1. A composition consisting of one or more Formula I compound salts according to the following structures:

or one or more Formula II compound salts according to the following structures:

(II)

(II)

(II)

wherein W at each instance independently is OH or PO$_4$, and wherein at least one W is PO$_4$.

2. The composition according to claim 1, wherein the composition consists of salts of one or more Formula I compounds according to the following structures:

(I)

(I)

(I)

3. The composition according to claim 1, wherein the composition consists of salts of one or more Formula II compounds according to the following structures:

(II)

(II)

(II)

(II)

4. A pharmaceutical composition comprising the composition according to claim 1 and a carrier.

5. A pharmaceutical composition comprising the composition according to claim 2 and a carrier.

6. A pharmaceutical composition comprising the composition according to claim 3 and a carrier.

* * * * *